United States Patent [19]

Stray-Gundersen

[11] Patent Number: 5,032,411

[45] Date of Patent: Jul. 16, 1991

[54] BEVERAGE COMPOSITIONS FOR HUMAN CONSUMPTION

[75] Inventor: James Stray-Gundersen, Dallas, Tex.

[73] Assignee: University of Texas System Board of Regents, Austin, Tex.

[21] Appl. No.: 485,609

[22] Filed: Feb. 27, 1990

[51] Int. Cl.$^5$ ............................................. A23L 1/304
[52] U.S. Cl. ..................................... 426/74; 426/590
[58] Field of Search ................................ 426/74, 590

[56] References Cited

U.S. PATENT DOCUMENTS

| | | | |
|---|---|---|---|
| 2,359,413 | 10/1944 | Freedman | 426/74 |
| 2,659,676 | 11/1953 | Howard | 426/74 |
| 3,657,424 | 4/1972 | Donald et al. | |
| 3,697,287 | 10/1972 | Winitz | 426/74 |
| 3,809,773 | 5/1974 | Bookwalter | |
| 3,950,546 | 4/1976 | Hill | 426/73 |
| 3,950,547 | 4/1976 | Lamar | 426/74 |
| 3,958,017 | 5/1976 | Morse | 426/72 |
| 4,042,684 | 8/1977 | Kahm | |
| 4,214,996 | 7/1980 | Buddemeyer | 426/74 |
| 4,309,417 | 1/1982 | Staples | |
| 4,312,856 | 1/1982 | Korduner et al. | |
| 4,322,407 | 3/1982 | Ko | |
| 4,448,770 | 5/1984 | Epting, Jr. | |
| 4,551,342 | 11/1985 | Nakel et al. | |
| 4,592,909 | 6/1986 | Winer et al. | |
| 4,649,051 | 3/1987 | Gyllang et al. | |
| 4,737,375 | 4/1988 | Nakel et al. | |
| 4,738,856 | 4/1988 | Clark | |
| 4,786,510 | 11/1988 | Nakel | 426/74 |
| 4,830,862 | 5/1989 | Braun et al. | |
| 4,853,237 | 8/1989 | Prinkkela | 426/590 |
| 4,871,550 | 10/1989 | Millman | |
| 4,874,606 | 10/1989 | Boyle | 426/74 |
| 4,919,963 | 4/1990 | Heckert | 426/599 |

FOREIGN PATENT DOCUMENTS 896486 3/1972 Canada .
2037565 11/1979 United Kingdom .

*Primary Examiner*—Carolyn Paden
*Attorney, Agent, or Firm*—Johnson & Gibbs

[57] ABSTRACT

Hypotonic beverage compositions and beverage concentrates adapted for oral administration of water, physiologically essential electrolytes, nutrient minerals, carbohydrates, and other ingredients to a human body. The hypotonic beverage composition comprises an aqueous solution, either carbonated or non-carbonated, of iron, electrolytes, carbohydrates, low-caloric sweetener, and edible acid components in ranges as stated.

58 Claims, No Drawings

BEVERAGE COMPOSITIONS FOR HUMAN CONSUMPTION

FIELD OF INVENTION

The present invention relates to carbonated and non-carbonated beverage compositions and beverage concentrates adapted for oral administration of water, physiologically essential electrolytes, nutrient minerals, carbohydrates, and other ingredients to a human body, and more particularly, the present invention relates to hypotonic beverage compositions and beverage concentrates.

Physical activity, such as exercise, particularly in the heat, places a great metabolic demand on a human body. During exercise, sweat is lost from the body, which can produce a state of dehydration or hypohydration. Dehydration, is associated with a reduction in the plasma volume. Associated with dehydration is an impairment of body heat dissipation and endurance performance. Although body electrolytes are also lost through perspiration, the net concentration of electrolytes per unit volume of body fluid actually increases. This is because perspiration causes a proportionally greater loss of water in comparison to the loss of body electrolytes. In addition, physical activity places a demand on the body's carbohydrate stores, such as muscle glycogen, liver glycogen, and plasma glucose. Loss of water, redistribution and loss of electrolytes, and the depletion of endogenous carbohydrate stores are primary causes of fatigue which impairs one's work capacity. To maintain the body's physical capabilities, it is essential that water, electrolytes, carbohydrate, and other nutrients be provided in a timely and appropriate manner. Fluid replacement during physical activity has been shown to be effective in preventing dehydration and hyperthermia.

Various illnesses and operations often cause a state of hypohydration. Thus, fluid replacement is also essential during illness and during post-operation recovery periods. Moreover, general activity requires fluid replacement as well.

The quantity of fluid and carbohydrate that can be effectively absorbed is governed by the gastric emptying rate and the absorptive efficiency once the fluid and carbohydrate enter the small intestine. The gastric emptying rate is the rate at which stomach contents empty from the stomach. After the consumption of a carbohydrate-containing drink, the drink will immediately enter the stomach. Minimal absorption of water or carbohydrates occurs in the stomach, however. The absorption occurs only after the passage of the drink through the pylorus into the intestines. The stomach or gastric emptying rate into the intestines is thus an essential limiting factor for the rapid replacement of fluids to the body. It has been proposed that the pylorus is normally closed and its opening is essentially controlled by the osmotic pressure of the stomach contents. The hypothesis is that the lower the osmotic pressure of the contents in the stomach, the more rapid the contents are emptied into the intestines. The proposed mechanism is that the emptying of water solutions into the small intestine has been related to osmoreceptors residing in the duodenum. The osmoreceptors monitor the discharge of a fluid from the stomach. When the osmolality of the fluid is high, an osmotic gradient is established that serves to reduce water penetration to the receptors. The resulting shrunken vesicle then slows gastric emptying.

To enhance endurance performance, commercial fluid replacement drinks often contain a simple carbohydrate, such as glucose or fructose, as a supplementary energy source. Unfortunately, there is a trade-off between the goal of rapid fluid replacement and the goal of energy supplementation when a person consumes a carbohydrate-containing drink. As the carbohydrate concentration of a drink increases, its osmolality increases, thereby reducing its gastric emptying rate. Consequently, the rate of fluid replacement to the system is decreased.

Osmolality is defined as the number of dissolved particles in a unit volume of water solution. Osmolarity is defined as the number of dissolved particles in a unit weight of water solution. As a practical matter, osmolality and osmolarity have numerical values which are very close in the ranges involved in the present invention. A solution that has 1/1000 of an osmol dissolved per kilogram has a concentration of 1 milliosmos ("mOs") per kilogram. An osmol is the number of particles in 1 gram molecular weight of undissociated solute. Tonicity is a measure of the osmotic pressure of a solution relative to the osmotic pressure of the blood fluids. It is to be understood that the osmotic pressure of the body varies somewhat from one person to the other person. A hypotonic solution is a solution of lower osmotic pressure or tonicity than that of blood. The osmolality of a hypotonic solution is usually in the range of about 80–250 mOs/l. An isotonic solution has the same tonicity as blood. Here, the osmolality usually ranges from about 280 to about 310 mOs/l. A hypertonic solution is a solution of greater tonicity than blood. It normally has an osmolality range of about 310–440 mOs/l. Water has the osmolality of about 10–20 mOs/l. Water and hypotonic beverages are most effective for rapidly replacing bodily fluids.

Carbohydrate-containing drinks raise blood sugar concentration, and therefore increases plasma insulin levels which cause readjustment of the metabolism of the liver in a glycogen-saving direction. Insulin drives glucose out of the blood and into cells. If the rise in blood sugar is rapid, it provides a large release of insulin which drives the blood sugar level lower than it was to start with. Different carbohydrates have differing abilities to stimulate insulin secretion.

Different compositions for beverages have been described in related references.

U.S. Pat. No. 3,657,424 to Donald et al., issued Apr. 18, 1972, teaches a citrus juice fortified with sodium, calcium and chloride ions beyond what are naturally present in the juice. The ions are added to supplement the requirements of individuals having diminished amounts of these substances present in his or her body fluids.

U.S. Pat. No. 4,042,684 to Kahm, issued Aug. 16, 1977, discloses a beverage for supplementing the dietetic requirements of sugar and essential salts in a mammalian body depleted through physical activity. The beverage contains an aqueous solution of fructose, glucose, sodium chloride, potassium chloride, and free citric acid. The patent teaches to include glucose in the beverage in an amount at least twice that of fructose.

U.S. Pat. No. 4,309,417 to Staples, issued Jan. 5, 1982, describes a protein fortified isotonic beverage containing sodium ions, potassium ions, chloride ions, phosphate ions, and a sweetener. Most of the electrolytes needed in the beverage are provided by the whey protein concentrate added to the beverage. The osmolarity of the beverage ranges from about 140 to about 375 mOs/kg.

U.S. Pat. No. 4,312,856 to Korduner et al., issued Jan. 26, 1982, discloses a beverage product adapted for rapid replacement of liquid and carbohydrate in the human body during periods of heavy muscle work. The product is a hypotonic solution that is free of monosaccharide. It contains mineral salts, soluble oligosaccharides and/or polysaccharides.

U.S. Pat. No. 4,322,407 to Ko, issued Mar. 30, 1982, teaches a chemical composition for reconstituting with water to provide electrolyte drink. The drink consists of sodium, potassium, magnesium, chloride, sulfate, phosphate, citrate, sucrose, dextrose, ascorbic acid, and pyridoxine.

U.S. Pat. No. 4,448,770 to Epting, Jr., issued May 15, 1984, describes a dietetic beverage adapted for human consumption to maintain the balance of body fluids during periods of fluid depletion or potassium depletion. The beverage contains potassium ions, calcium ions, magnesium ions, and sucrose. The amount of sucrose present ranges from 5 to 10 ounces per gallon of the beverage.

U.S. Pat. No. 4,551,342 to Nakel et al., issued Nov. 5, 1985, describes a beverage suitable for carbonated soft drinks having a pH range from about 2.5 to about 6.5. The beverage contains a mixture of calcium, potassium, and magnesium cations, defined by a first regression formula. Also included are acids, such as citric, malic, succinic and phosphoric acids, defined by a second regression formula.

U.S. Pat. No. 4,592,909 to Winer et al., issued June 3, 1986, teaches a water based drink formulated for consumption by an athlete. The drink contains water to which have been added salts of sodium, potassium, calcium, and magnesium. The drink does not contain any sugar so that the osmolality of the drink can be kept low.

U.S. Pat. No. 4,649,051 to Gyllang et al., issued Mar. 10, 1987, discloses a beverage product adapted for administration of water and carbohydrates to a human body. The drink is monosaccharide-free.

U.S. Pat. No. 4,737,375 to Nakel et al., issued Apr. 12, 1988, teaches beverages and beverage concentrates nutritionally supplemented with mixtures of citric, malic, phosphoric acids, and also significant levels of solubilized calcium. The beverages and concentrates are substantially free of sugar alcohol.

U.S. Pat. No. 4,738,856 to Clark, issued Apr. 19, 1988, teaches a beverage solution containing ions of calcium, magnesium and potassium. The beverage also contains a sweetener and a stabilizer.

U.S. Pat. No. 4,830,862 to Braun et al., issued May 16, 1989, describes beverages and beverage concentrates supplemented with significant levels of solubilized calcium and low levels of sulfate and chloride ions. They also contain acids selected from phosphoric acid, citric acid, malic acid, fumaric acid, adipic acid, gluconic acid, and lactic acid, as well as mixtures of these acids.

U.S. Pat. No. 4,871,550 to Millman, issued on Oct. 3, 1989, teaches a nutrient composition. The composition contains free amino acids, carbohydrates, vitamins, minerals and trace elements, electrolytes, and flavoring aids.

Canadian Patent No. 896486 to Babagan et al., issued on Mar. 28, 1972, teaches an essentially isotonic beverage containing dextrose and electrolytes in contrast to the customary beverages that utilize sucrose.

A wide variety of electrolyte and sport drinks are available in the market. These drinks allegedly replenish water, carbohydrates, essential electrolytes, and other ingredients lost from a human body through dehydration.

Gatorade ® Thirst Quencher, marketed by Stokely-Van Camp, Inc., contains about 6% of sucrose and glucose. It also contains sodium, potassium, chloride, and phosphorus. The drink has an osmolality in the range of between 280–360 mOs/liter.

Exceed ® Fluid Replacement & Energy Drink, marketed by Ross Laboratories, contains about 7% of glucose polymers and fructose. It also includes sodium, potassium, calcium, magnesium, and chloride. The drink has an osmolality of 250 mOs/liter.

Quickkick ®, marketed by Cramer Products, Inc., contains about 4.7% of fructose and sucrose. The drink is also provided with sodium, potassium, calcium, chloride, and phosphorus. The drink has an osmolality of 305 mOs/liter.

Sqwincher ® the Activity Drink, marketed by Universal Products Inc., contains glucose, fructose, sodium, potassium, calcium, magnesium, phosphorus, chloride, and Vitamin C. The drink has an osmolality of 470 mOs/liter.

10-K TM, marketed by Beverage Products, Inc., contains sucrose, glucose, fructose, sodium, potassium, Vitamin C, chloride, and phosphorus. The drink has an osmolality of 350 mOs/liter.

USA Wet TM, marketed by Texas Wet, Inc., contains sucrose, sodium, potassium, chloride, and phosphorus. The drink has an osmolality of 450 mOs/liter.

It is seen that almost all of these beverages are hypertonic, having osmolality of at least above 250 mOs/liter. High osmolality slows the gastric emptying, and consequently such drinks reduce the rate of fluid replacement to the body. Further, most of these beverages contain large amount of glucose which triggers a sudden and transient insulin response causing further imbalance of carbohydrate metabolism in the body. Moreover, many of the commercial beverages suffer from poor taste. Thus, they do not, in fact, satisfy the body needs completely by rapidly replenishing water, electrolytes, carbohydrates, and other essential constituents which are lost through dehydration. The present invention overcomes many of the prior art problems as discussed above.

SUMMARY OF THE INVENTION

It is therefore an object of the present invention to provide a new and improved hypotonic beverage composition and concentrate.

It is another object of the present invention to provide a hypotonic beverage composition especially formulated to rapidly replenish water, physiologically essential electrolytes, nutrient minerals, and sweeteners such as carbohydrates or non-caloric sweeteners to a person who has lost water through dehydration caused by exercise, heat, or illness.

It is still another object of the present invention to provide a beverage composition that will minimize the disturbance of the metabolic balance in the body of a person.

It is another object of the present invention to provide a beverage composition that contains an antioxidant.

It is also an object of the present invention to provide a beverage composition that contains essential physiological electrolytes.

It is yet another object of the present invention to provide a beverage composition that can deliver a carbohydrate energy source to the body of a person and yet minimally stimulate insulin secretion.

It is still another object of the present invention to provide a beverage composition that provides immediate as well as sustained carbohydrate energy source to the body.

It is yet another object of the present invention to provide a carbonated hypotonic beverage composition.

It is a further object of the present invention to provide a palatable beverage composition that is supplemented with iron.

It is also an object of the present invention to provide a beverage composition that can be administered to various mammals to prevent dehydration, loss of electrolytes, and nutrient minerals during periods of activity.

It is further an object of the present invention to provide a beverage composition adapted for oral administration of water, physiologically essential electrolytes, nutrient minerals, and sweeteners to a human body containing: from about 0.4 to about 0.8 ppm of solubilized iron; from about 3 to about 50 milliequivalents ("meq") of an electrolyte per liter of the beverage composition; from about 0 to about 8 weight percent, based on the total weight of the beverage composition, of a carbohydrate; from 0 to about 14 weight percent, based on the total weight of the beverage composition, of a low-caloric sweetener; sufficient amount of an edible acid component to adjust the pH of the beverage composition to a range from about 2 to about 6.5; the beverage composition having an osmolality of from about 100 to about 270 mOs/l; and a sufficient amount of water necessary to establish the foregoing properties.

It is also an object of the present invention to provide a concentrate for use in forming a final aqueous beverage containing an admixture of materials in amounts and ratios such that when constituted with water, carbonated or non-carbonated, to form the final aqueous beverage, the following conditions and proportions are obtained: from about 0.4 to about 0.8 ppm of solubilized iron; from about 3 to about 50 meq. of an electrolyte per liter of the final aqueous beverage; from about 0 to about 8 weight percent, based on the total weight of the final aqueous beverage, of a carbohydrate; from about 0 to about 14 weight percent, based on the total weight of the final aqueous beverage, of a low-caloric sweetener; a sufficient amount of an edible acid component to adjust the pH of the final aqueous beverage to a range from about 2 to about 6.5; and the final aqueous beverage having an osmolality of from about 100 to about 270 mOs/l.

It is a further object of the present invention to provide an essentially dry mixture suitable for constituting with water, carbonated or non-carbonated, to form a final beverage for oral administration of water, physiologically essential electrolytes, nutrient minerals, and carbohydrates to a human body, the dry mixture comprising: from about 0.4 to about 0.8 ppm of iron; from about 8 to about 12 meq. of a potassium cation component per liter of the final aqueous beverage; from about 8 to about 12 meq. of a sodium cation component per liter of the final aqueous beverage from about 75 to about 200 mg of Vitamin C per liter of the final aqueous beverage; from about 20 to about 60 I.U. of Vitamin E per liter of the final aqueous beverage; from about 1 to about 5 weight percent, based on the total weight of the final aqueous beverage, of crystalline fructose; from about 3 to about 6 weight percent, based on the total weight of the final aqueous beverage, of maltodextrin; a sufficient amount of an edible acid component such that when the essentially dry mixture is constituted with water to give the final aqueous beverage the pH in a range of from about 2 to about 6.5; and the final aqueous beverage having an osmolality of from about 100 to about 270 mOs/l.

DETAILED DESCRIPTION OF THE PRESENT INVENTION

The present invention is based on a number of new discoveries and combinations of such discoveries with known scientific data which are summarized below:

(1) The main function of a fluid replacement beverage is to rapidly replenish water to a person who has lost water through perspiration and respiratory loss.

(2) A beverage must first be emptied from the stomach to the intestine before the beverage can be absorbed by the body. Thus, the rate of absorption is dependent upon the stomach emptying rate.

(3) A hypotonic beverage empties from the stomach faster than an isotonic beverage or a hypertonic beverage does.

(4) A hypotonic beverage with an osmolality of about 140-150 mOs/liter, which is approximately one half of that of the blood, empties very rapidly from the stomach.

(5) The Body absorbs water about as rapidly as it absorbs a solution containing physiological electrolytes and 6% glucose.

(6) The performance of an athlete can be enhanced if blood glucose level in the body is maintained during exercise.

(7) One particle of dissolved polysaccharide, such as maltodextrin, increases the osmolality of the solution as much as one particle of dissolved simple saccharide does. When digested in the body, however, the polysaccharide particle will provide a greater caloric benefit than the particle of simple saccharide will.

(8) An orally ingested simple saccharide usually provides the most immediate energy to the body.

(9) An orally ingested complex saccharide usually provides a more sustained energy release to the body.

(10) Oral ingestion of relatively dilute carbohydrate beverage is sufficient to maintain blood glucose level during exercise.

(11) Fructose does not cause as rapid or as great a release of insulin in a body as a sucrose or a dextrose does.

(12) Sweat is hypotonic and contains very small amount of physiological electrolytes.

(13) Sweat contains an extremely small amount of iron.

(14) Supplementation of some physiological electrolytes is more important for people participating in long duration physical activities than for people participating in a short duration of physical activities.

(15) The most common nutritional deficiencies in developed countries are iron and calcium.

(16) Vitamin C promotes the absorption of iron into the body.

(17) A beverage containing excessive amounts of iron tends to give an unpleasant taste. The unpleasant taste, however, can be masked by reducing the amount of iron and carefully balancing the relative ratios of different ingredients in the beverage.

(18) Cramping resulting from exhaustive physical activity appears to be associated with an imbalance of physiological electrolytes, such as potassium, magnesium, bicarbonates, and phosphates.

(19) Strenuous physical activity induces damages in muscle cell membranes. The micro trauma is thought to be aggravated by oxygen radicals produced in the body during strenuous exercise.

(20) Both Vitamin C and Vitamin E are thought to be antioxidants and may reduce damage caused by oxygen radicals.

(21) Beverages with acidic pH tend to preserve better than beverages with alkaline pH.

(22) Beverages with acidic pH also tend to be more palatable than beverages with alkaline pH.

(23) Vitamin $B_{12}$ is thought to be an anabolic stimulant.

(24) Caffeine is a central nervous system stimulant.

(25) One can usually consume more, in quantity, of a carbonated beverage than a non-carbonated beverage.

The term "beverage composition" as used herein denotes a composition that is single-strength and ready to drink, that is, drinkable. As used herein, "beverage concentrate" refers to a concentrate that is either in liquid form or in essentially dry mixture form. The essentially dry mixture can be in the form of either a powder or a tablet. The concentrate is usually formulated to provide a drinkable beverage composition or a final beverage when constituted or diluted with water, either carbonated or non-carbonated.

One important aspect of the present invention is to provide a hypotonic beverage that has a rapid gastric emptying rate. The hypotonic beverage of the present invention has an osmolality that is lower than that of blood serum. The hypotonicity of the beverage is controlled by the types, quantities, and ratios of the ingredients added to the beverage. The osmolality of the beverage is maintained within the range of from about 100 to about 270 mOs/l. Preferably, the osmolality of the beverage is from about 100 to about 200 mOs/l. The beverage of the present invention is formulated so that it can rapidly replenish water, physiological essential electrolytes, nutrient mineral, and carbohydrates to people who have lost fluid from the body and who are in need of fluid replenishment. The need may arise from any kind of dehydration. The beverage is also formulated for people to consume before, during, or after engaging in physical activity. Broadly, the beverage contains a solubilized iron, essential physiological electrolytes, a sweetener such as a carbohydrate and/or a low-caloric sweetener, and an edible acid component. The edible acid component is necessary to give the beverage an acidic pH, in a range of from about 2 to about 6.5.

Among the major physiological electrolytes are sodium, potassium, chloride, calcium, and magnesium. The electrolytes and ionic components for the present invention are usually obtainable from their corresponding water-soluble and non-toxic salts. Unless otherwise defined, the amount of electrolytes or ionic components in the beverage is based on those present in the final drinkable beverage composition. Some of the less soluble salts must be "solubilized" in water, or in water having an acidic pH, in order to be useful in the present invention. For example, "solubilized calcium" means calcium ions dissolved. The ionic components indicate the components obtained when dissolved in water or acidified water.

The sodium ion component can be obtained from any readily available sodium salt, such as the chloride, carbonate, bicarbonate, citrate, phosphate, hydrogen phosphate, tartrate, benzoate and the like, or a combination thereof. The sodium ions are preferably present in the drinkable beverage composition of the present invention in an amount in the range of from about 8 to about 12 meq. per liter of the drinkable beverage composition, and more preferably in a range of from about 9 to about 11 meq. per liter of the drinkable beverage composition.

Likewise, the potassium ion component can be provided by any salt such as the chloride, bicarbonate, citrate, phosphate, hydrogen phosphate, tartrate, sorbate and the like, or a combination thereof. The potassium ions are preferably present in the drinkable beverage composition of the present invention in an amount in the range of from about 8 to about 12 meq. per liter of the drinkable beverage composition, and more preferably in a range of from about 9 to about 11 meq. per liter of the drinkable beverage composition.

The chloride ion component can be provided by a salt such as sodium chloride or potassium chloride. Preferably, the chloride ions should be present in the drinkable beverage composition of the present invention in an amount in the range of from about 8 to about 12 meq. per liter of the drinkable beverage composition, and more preferably in the range of from about 9 to about 11 meq. per liter of the drinkable beverage composition.

The bicarbonate ion component used in the present invention can be obtained from their corresponding sodium or potassium salts, among others. The bicarbonate ions are preferably present in the drinkable beverage composition of the present invention in an amount in the range of from about 8 to about 16 meq. per liter of the drinkable beverage composition, and more preferably in a range of from about 10 to about 14 meq. per liter of the drinkable beverage composition.

The phosphate ions needed for the present invention can be obtained from dissolution of hydrated disodium hydrogen phosphate and hydrated sodium dihydrogen phosphate in an aqueous solution. The phosphate ions are preferably present in the drinkable beverage composition of the present invention in an amount in the range of from about 3 to about 15 meq. per liter of the drinkable beverage composition, and more preferably in a range of from about 10 to about 14 meq. per liter of the drinkable beverage composition.

The solubilized iron for the present invention can be obtained from any suitable ferrous salts, such as ferrous sulfate, ferrous fumarate, ferrous gluconate, or mixture thereof. The solubilized iron is preferably present in the drinkable beverage composition of the present invention in an amount in the range of from about 0.4 to about 0.8 parts per million ("ppm") of the drinkable beverage composition, and more preferably in a range of from about 0.5 to about 0.7 ppm of the drinkable beverage composition. The amount of solubilized iron selected is an amount that is below a subjective taste threshold.

The solubilized magnesium for the present invention can be obtained from a salt such as magnesium citrate, magnesium oxide, magnesium aspartate, magnesium chloride, or magnesium sulfate. The magnesium ions are preferably present in the drinkable beverage composition of the present invention in an amount in the range of from about 1 to about 5 meq. per liter of the drinkable beverage composition, and more preferably in a range of from about 1 to about 3 meq. per liter of the drinkable beverage composition.

The solubilized calcium used in the present invention can be supplied by calcium carbonate, calcium phosphate, calcium hydrogen phosphate, calcium dihydrogen phosphate, calcium hydroxide, calcium chloride dehydrate, calcium sulfate, as well as the respective sour salts of calcium, such as, calcium citrate, calcium malate, calcium ascorbate, or calcium orotate, and mixture thereof. The calcium ions are preferably present in the drinkable beverage composition of the present invention in an amount in the range of from about 1 to about 5 meq. per liter of the drinkable beverage composition, and more preferably in a range of from about 1 to about 3 meq. per liter of the drinkable beverage composition.

Vitamin C used in the present invention either is supplied by ascorbic acid or its alkaline salt. Preferably, Vitamin C is present in the drinkable beverage composition of the present invention in an amount in the range of from about 75 to about 200 mg per liter of the drinkable beverage composition, and more preferably, in an amount in the range of from about 80 to about 120 mg per liter of the drinkable beverage composition.

Vitamin E for the present invention is supplied by dl-$\alpha$-tocopherol acetate. Preferably, Vitamin E is present in the drinkable beverage composition or concentrate of the present invention in an amount in the range of from about 20 to about 60 international units ("I.U."), and more preferably, in an amount in the range of from about 30 to about 50 I.U. per liter of the drinkable beverage.

Vitamin $B_{12}$ can also be added to the drinkable beverage composition or the concentrate of the present invention. Preferably, when present, it is in the amount of from about 1 to about 5 ug per liter of the drinkable beverage composition, and preferably from about 2 to about 3 ug per liter of the drinkable beverage composition.

The edible acid component of the present invention can be selected from phosphoric acid, citric acid, malic acid, succinic acid, tartaric acid, fumaric acid, and mixture thereof. In the case of malic acid and succinic acid, they can be wholly or partly substituted thereof. The acids can be in their undissociated forms or as their respective "sour salts," such as phosphate, dihydrogen phosphate, citrate, malate, or the combination thereof. Preferably, the pH range of the drinkable beverage composition is from about 2 to about 6.5, and more preferably from about 3 to about 5.

The phosphate and the citrate ions present in the beverage compositions or concentrates can also function as a buffer system to maintain the drinkable beverage composition within a pH range.

The present invention also contains a soluble carbohydrate. Carbohydrate is a sweetener as well as an energy source. As used herein, the term "carbohydrate" refers to monosaccharides, oligosaccharides, complex polysaccharides, or mixtures thereof. The monosaccharides, include tetroses, pentoses, hexoses, and ketohexoses. Examples of hexoses are aldohexoses such as glucose and dextrose, known as grape sugar. The amount of dextrose used for the drinkable beverage composition of the present invention preferably is in a range of from about 1 to about 2 weight percent, based on the total weight of the beverage composition, and more preferably from about 1.5 to about 2 weight percent of the total weight of the beverage composition. Fructose, known as fruit sugar, is a ketohexose. Preferably, the range of fructose present in the present drinkable beverage composition is from about 1 to about 3 weight percent of the total weight of the beverage composition, and more preferably from about 1 to about 2 weight percent of the total weight of the beverage composition. For the essentially dry mixture suitable for constituting with water to form a final aqueous beverage, the preferable range of crystalline fructose is from about 1 to about 4 weight percent, based on the total weight of the final aqueous beverage, and more preferably in the range of from about 1 to about 2 weight percent of the total weight of the final aqueous beverage. An important class of oligosaccharide is disaccharide. An example of a disaccharide is sucrose, known as cane sugar or beet sugar. Preferably, the amount of sucrose present in the drinkable beverage composition of the present invention is below 0.2 weight percent of the total weight of the beverage composition, and more preferably in the range of from about 0.1 to about 0.2 weight percent, based on the total weight of the drinkable beverage composition. One of the complex polysaccharides usable for the present invention is maltodextrin. Maltodextrins are a form of complex carbohydrate molecule several glucose units in length. They are spray-dried carbohydrate ingredients made by controlled hydrolysis of corn starch. Maltodextrin M-100 has a very low hygroscopicity, very low reducing sugars and browning reactions. It has very slight sweetness and has approximately 30% true solubility. The dextrose equivalence ("D.E.") of maltodextrin M-100 is approximately 10. D.E. provides a good index of the degree of starch polymer hydrolysis. This index is the percent conversion as determined by quantitative analysis of end-group reducing sugars. The Food and Drug Administration defines maltodextrin $(C_6H_{12}O_5)_nH_2O$ (CAS Reg. No. 9050-36-6) as a nonsweet, nutritive saccharide polymer that consists of D-glucose units linked primarily by alpha-1,4-bonds. Generally, maltodextrins have a D.E. of less than 20. The preferred range of maltodextrin for the drinkable beverage composition is between about 3 to about 6 weight percent of the total weight of the drinkable beverage composition, and more preferably from about 2 to about 4 weight percent, based on the total weight of the drinkable beverage composition.

For diet beverages, non-caloric or low-caloric sweeteners can be used. The terms "non-caloric" and "low-caloric" are used interchangeable. The low-caloric sweeteners can be derived either from natural origins or from synthetic sources. Examples of such non-caloric or low-caloric carbohydrate sweeteners include, but are not limited to, saccharin, cyclamates, acetosulfam, sorbitol, xylitol, L-aspartyl-L-phenyl-alanine ester (e.g. aspartame), L-aspartyl-D-alanine alkyl amides disclosed in European Patent Application No. 34,876 to Pfizer, published Sept. 2, 1981 (herein incorporated by reference), L-aspartyl-L-1-hydroxymethylalkaneamide sweeteners disclosed in U.S. Pat. No. 4,338,346 to Brand, issued Dec. 21, 1982 (herein incorporated by reference), L-aspartyl-1-hydroxyethylalkaneamide sweeteners disclosed in U.S. application Ser. No. 277,307 to G. P. Rizzi, filed June 25, 1981, now U.S. Pat. No. 4,423,029, issued Dec. 27, 1983 (herein incorporated by reference), and the like. The amount of the non-caloric sweetener used depends on the particular sweetener, or mixture of sweeteners, and the sweetness intensity desired. Generally, the non-caloric or low-caloric sweetener ranges from about 0.5 to about 14 weight percent, based on the total weight of the drinkable beverage composition. In diet drinks, if desired, one percent weight of fructose, based on the total weight of the drinkable beverage composition, can be used. Preferably, the diet beverage composition should not contain any maltodextrin.

As used herein, Brix is a measure of the soluble solids in a liquid as measured by refractometer. The Brix can be expressed in weight percent.

Caffeine can be added to the beverage composition of the present invention if desired. The preferred range of added caffeine is from about 100 to about 200 mg per liter of the drinkable beverage composition.

A flavoring additive of the beverage composition and the concentrate of the present invention includes a flavor selected from fruit flavors, botanical flavors, and mixtures thereof. As used herein, the term "fruit flavor" denotes flavors derived from the natural edible reproductive parts of seed plants as well as synthetically prepared flavors made to simulate fruit flavors derived from natural sources. Preferred flavoring additives are citrus flavors, such as orange flavor, lemon flavor, lime flavor, fruit punch, and mixtures thereof. Other flavors, such as grape flavor, cherry flavor, apple flavor, and mixtures thereof, can also be used. The amount of soluble flavor additive used depends upon the flavor or flavors selected, the flavor impression desired, and the form of flavor additive used. When a concentrated flavor is used as an additive, the amount of flavor additive can vary from about 0.05 to about 0.5 weight percent based on the total weight of the drinkable beverage composition.

If desired, coloring agents can also be added into the drinkable beverage compositions or beverage concentrates of the present invention. Any soluble coloring agents approved for food use can be utilized for the present invention.

When desired, preservatives, such as potassium sorbate and sodium benzoate, can be added into the drinkable beverage composition or beverage concentrate of the present invention. Amounts ranging from abut 0.01 to about 15 weight percent of the drinkable beverage composition can be used.

The drinkable beverage composition may be prepared by mixing together all of the ingredients. The mixture is then dissolved in water and agitated with a mechanical stirrer until all of the ingredients have gone into solution. It may be necessary for the solution to be heated to a temperature between about 50° C. and about 100° C. to get all the ingredients dissolved. The preservative can then be added. After the mixture has been adjusted to a desired pH with an acid component, the beverage may be bottled, capped, and pasteurized at about 75° C. for about 20 minutes.

One way to prepare the concentrate form of the liquid beverage would be to start with less than the required volume of the liquid solvent that is used in the preparation of the drinkable beverage composition. Another way would be to partially dehydrate the finally prepared drinkable beverage composition to remove only a portion of the liquid solvent and any other volatile liquids present. Dehydration can be accomplished in accordance with a well known procedure, such as evaporation under vacuum. The concentrate can be in the form of a relatively thick, syrupy liquid or a solid. The solid can be in the form of an essentially dry powder or a tablet. The concentrate can later be constituted with a proper amount of water to make the final drinkable beverage composition.

Carbon dioxide can be introduced either into the water to be mixed with the beverage concentrate, or into the drinkable beverage composition, to achieve carbonation. The carbonated beverage composition can then be stored in a container, such as a bottle or a can and then sealed. See L. F. Green, Development in Soft Drinks Technology, Vol. 1, pp. 102-107, Applied Science Publishers Ltd., 1978, herein incorporated by reference. The amount of carbon dioxide introduced into the beverage composition depends upon the particular flavor system used and the amount of carbonation desired. Usually, carbonated beverages of the present invention contain from about 1.0 to about 4.5 volumes of carbon dioxide. Preferred carbonated beverages contain from about 2 to about 3.5 volumes of carbon dioxide.

The essentially dry mixture of the beverage composition can be prepared by blending the proper amounts and ratios of all the required dry ingredients together. Alternatively, the finally prepared drinkable beverage composition can be dehydrated to give the essentially dry mixture of the beverage composition. An edible binding agent, such as starch, can be added to a powder form of the beverage composition and the resulting mixture compacted into tablets. The essentially dry mixture, either as powder, granules or tablets, can later be dissolved in a proper amount of water, carbonated or non-carbonated, to make the final drinkable beverage composition.

EXAMPLE I

A drinkable beverage composition was prepared containing the following ingredients:

| Ingredients | Amount |
|---|---|
| Iron | 0.59 ppm (0.010 meq./l) |
| Vitamin C | 100 mg/l |
| Potassium | 10.3 meq./l |
| Sodium | 10 meq./l |
| Calcium | 6 meq./l |
| Chloride | 10 meq./l |
| Phosphates | 9 meq./l |
| Bicarbonate | 12 meq./l |
| Magnesium | 2 meq./l |
| Vitamin E | 38 I.U./l |
| Maltodextrin M-100 | 2% |
| Fructose | 2.45% |
| Dextrose | 1.87% |
| Sucrose | 0.13% |
| Osmolality | 244 mOs/l |
| Brix | 7.2 |
| pH | 3.16 |
| Acidity (75% Phosphoric acid and citric acid) | 48.4* |

The letter "l" denotes liter.
The percentage given was the weight percent of the ingredient based on the total weight of the final drinkable beverage composition.
*the "acidity" is expressed as volume in ml of 0.1 N NaOH required to adjust the beverage composition to a pH of 8.3.

EXAMPLE II

An essentially dry mixture of the beverage composition was prepared by blending the following ingredients so that when constituted or dissolved in water to give a final beverage, the following properties were established:

| Ingredients | Amount |
| --- | --- |
| Iron | 0.59 ppm (0.010 meq./l) |
| Vitamin C | 100 mg/l |
| Potassium | 10 meq./l |
| Sodium | 10 meq./l |
| Calcium | 6 meq./l |
| Chloride | 10 meq./l |
| Phosphates | 4 meq./l |
| Bicarbonate | 12 meq./l |
| Magnesium | 2 meq./l |
| Vitamin E | 38 I.U./l |
| Maltodextrin M-100 | 4% |
| Crystalline Fructose | 3.1% |
| Osmolality | 172 mOs/l |
| Brix | 7.5 |
| pH | 3.34 |
| Acidity (Citric Acid) | 41.9* |

The letter "l" denotes liter.
The percentage given is the weight percent of the ingredient based on the total weight of the final beverage.
*The "acidity" is expressed as volume in ml of 0.1 N NaOH required to adjust the beverage composition to a pH of 8.3.

The invention now being fully described, it will be apparent to one of ordinary skill in the art that many changes and modifications can be made thereto without departing from the spirit or scope of the invention as defined in the following claims.

I claim:

1. An aqueous beverage composition adapted for oral administration of water, physiologically essential electrolytes, nutrient minerals, and sweeteners to a human body comprising:
   from about 0.4 to about 0.8 ppm of solubilized iron;
   from about 3 to about 50 meq. of an electrolyte per liter of said beverage composition;
   from about 0 to about 8 weight percent, based on the total weight of said beverage composition, of a carbohydrate;
   from about 0 to about 14 weight percent, based on the total weight of said beverage composition, of a low-caloric sweetener;
   a sufficient amount of an edible acid component to adjust the pH of said beverage composition to a range from about 2 to about 6.5;
   said beverage composition having an osmolality of from about 100 to about 270 mOs/l; and
   a sufficient amount of water necessary to establish the foregoing properties.

2. The beverage composition of claim 1 wherein said electrolyte is selected from a group consisting of sodium ions and potassium ions.

3. The beverage composition of claim 1 wherein said edible acid component comprises phosphoric acid.

4. The beverage composition of claim 1 wherein said edible acid component comprises citric acid.

5. The beverage composition of claim 1 wherein said water is carbonated.

6. The beverage composition of claim 1 wherein said carbohydrate comprises fructose.

7. The beverage composition of claim 1 wherein said carbohydrate comprises sucrose.

8. The beverage composition of claim 1 wherein said carbohydrate comprises maltodextrin.

9. The beverage composition of claim 1 further comprising Vitamin C.

10. The beverage composition of claim 9 wherein said Vitamin C is in an amount ranging from about 75 to about 200 mg per liter of said beverage composition.

11. The beverage composition of claim 1 further comprising Vitamin E.

12. The beverage composition of claim 11 wherein said Vitamin E is in an amount ranging from about 20 to about 60 I.U. per liter of said beverage composition.

13. The beverage composition of claim 1 further comprising an edible buffering component.

14. The beverage composition of claim 13 wherein said edible buffering component is selected from a group consisting of bicarbonate ions and phosphate ions.

15. The beverage composition of claim 1 further comprising a flavoring additive.

16. The beverage composition of claim 15 wherein said flavoring additive is present in an amount ranging from about 0.01 to about 1 weight percent based on the total weight of said beverage composition.

17. The beverage composition of claim 15 wherein said flavoring additive is a fruit flavored additive.

18. The beverage composition of claim 1 further comprising a preservative.

19. The beverage composition of claim 18 wherein said preservative is present in an amount ranging from about 0.01 to about 1 weight percent based on the total weight of said beverage composition.

20. The beverage composition of claim 18 wherein said preservative is potassium sorbate.

21. The beverage composition of claim 1 further comprising Vitamin $B_{12}$.

22. The beverage composition of claim 21 wherein said Vitamin $B_{12}$ is present in an amount ranging from about 1 to about 5 micrograms per liter of said beverage composition.

23. The beverage composition of claim 1 further comprising caffeine.

24. The beverage composition of claim 23 wherein said caffeine is present in an amount ranging from about 100 to about 200 mg per liter of said beverage composition.

25. An aqueous beverage composition adapted for oral administration of water, physiologically essential electrolytes, nutrient minerals, and carbohydrate to a human body, comprising:
   from about 0.4 to about 0.8 ppm of solubilized iron;
   from about 8 to about 12 meq. of potassium ions per liter of said beverage composition;
   from about 8 to about 12 meq. of sodium ions per liter of said beverage composition;
   from about 4 to about 8 meq. of solubilized calcium per liter of said beverage composition;
   from about 8 to about 12 meq. of chloride ions per liter of said beverage composition;
   from about 3 to about 15 meq. of phosphate ions per liter of said beverage composition;
   from about 1 to about 5 meq. of solubilized magnesium per liter of said beverage composition;
   from about 8 to about 16 meq. of bicarbonate ions per liter of said beverage composition;
   from about 75 to about 200 mg of Vitamin C per liter of said beverage composition;
   from about 20 to about 60 I.U. of Vitamin E per liter of said beverage composition;
   from about 0.5 to about 3 weight percent, based on the total weight of said beverage composition, of fructose;
   from about 1.3 to about 2 weight percent, based on the total weight of said beverage composition, of dextrose;

from 0.1 to about 0.2 weight percent, based on the total weight of said beverage composition, of sucrose;

from about 3 to about 6 weight percent, based on the total weight of said beverage composition, of maltodextrin;

a sufficient amount of an edible acid component to adjust the pH of said beverage composition to a range from about 3 to about 6;

a sufficient amount of an edible buffering component to maintain said pH;

said beverage composition having an osmolality of from about 100 to about 270 mOs/l; and a sufficient amount of water necessary to establish the foregoing properties.

26. The beverage composition of claim 25 wherein said water is carbonated.

27. The beverage composition of claim 25 further comprising Vitamin $B_{12}$.

28. The beverage composition of claim 27 wherein said Vitamin $B_{12}$ is present in an amount ranging from about 1 to about 5 micrograms per liter of said beverage composition.

29. The beverage composition of claim 25 further comprising caffeine.

30. The beverage composition of claim 29 wherein said caffeine is present in an amount ranging from about 100 to about 200 mg per liter of said beverage composition.

31. An aqueous beverage composition adapted for oral administration of water, physiologically essential electrolytes, nutrient minerals, and carbohydrates to a human body before, during, or after periods of physical activity, comprising:

from about 0.5 to about 0.7 ppm of solubilized iron;

from about 9 to about 11 meq. of potassium ions per liter of said beverage composition;

from about 9 to about 11 meq. of sodium ions per liter of said beverage composition;

from about 5 to about 7 meq. of solubilized calcium per liter of said beverage composition;

from about 9 to about 11 meq. of chloride ions per liter of said beverage composition;

from about 10 to about 14 meq. of phosphate ions per liter of said beverage composition;

from about 1 to about 3 meq. of solubilized magnesium per liter of said beverage composition;

from about 10 to about 14 meq. of bicarbonate ions per liter of said beverage composition;

from about 80 to about 120 mg of Vitamin C per liter of said beverage composition;

from about 30 to about 50 I.U. of Vitamin E per liter of said beverage composition;

from about 1 to about 2 weight percent, based on the total weight of said beverage composition, of fructose;

from about 1.5 to about 2 weight percent, based on the total weight of said beverage composition, of dextrose;

from 0.1 to about 0.2 weight percent, based on the total weight of said beverage composition, of sucrose;

from about 3 to about 6 weight percent, based on the total weight of said beverage composition, of maltodextrin;

a sufficient amount of an edible acid component to adjust the pH of said beverage composition to a range from about 3 to about 5;

said beverage composition having an osmolality of from about 100 to about 270 mOs/l; and a sufficient amount of water necessary to establish the foregoing properties.

32. A concentrate for use in forming a final aqueous beverage comprising an admixture of materials in amounts and ratios such that when constituted with water, carbonated or non-carbonated, to form said final aqueous beverage, the following conditions and proportions are obtained:

from about 0.4 to about 0.8 ppm of solubilized iron;

from about 3 to about 50 meq. of an electrolyte per liter of said final aqueous beverage;

from about 0 to about 8 weight percent, based on the total weight of said final aqueous beverage, of a carbohydrate;

from about 0 to about 14 weight percent, based on the total weight of said final aqueous beverage, of a low-caloric sweetener;

a sufficient amount of an edible acid component to adjust the pH of said final aqueous beverage to a range from about 2 to about 6.5; and said final aqueous beverage having an osmolality of from about 100 to about 270 mOs/l.

33. The concentrate of claim 32 wherein said electrolyte is selected from a group consisting of sodium ion component and potassium ion component.

34. The concentrate of claim 32 wherein said carbohydrate comprises fructose.

35. The concentrate of claim 32 wherein said carbohydrate comprises sucrose.

36. The concentrate of claim 32 wherein said carbohydrate comprises maltodextrin.

37. The concentrate of claim 32 wherein said edible acid component comprises citric acid.

38. The concentrate of claim 32 further comprising Vitamin C.

39. The concentrate of claim 38 wherein said Vitamin C is present in an amount ranging from about 75 to about 200 mg per liter of said final aqueous beverage.

40. The concentrate of claim 32 further comprising Vitamin E.

41. The concentrate of claim 40 wherein said Vitamin E is present in an amount ranging from about 20 to about 60 I.U. per liter of said final aqueous beverage.

42. The concentrate of claim 32 further comprising an edible buffering component.

43. The concentrate of claim 42 wherein said edible buffering component is selected from a group consisting of bicarbonate ion component and phosphate ion component.

44. The concentrate of claim 32 further comprising a flavoring additive.

45. The concentrate of claim 44 wherein said flavoring additive is present in an amount ranging from about 0.01 to about 1 weight percent based on the total weight of said final aqueous beverage.

46. The concentrate of claim 32 further comprising Vitamin $B_{12}$.

47. The concentrate of claim 46 wherein said Vitamin $B_{12}$ is present in an amount ranging from about 1 to about 5 micrograms per said liter of beverage composition.

48. The concentrate of claim 32 further comprising caffeine.

49. The concentrate of claim 48 wherein said caffeine is present in an amount ranging from about 100 to about 200 mg per liter of said final aqueous beverage.

50. The concentrate of claim 32 wherein said concentrate is in the form of a syrup.

51. The concentrate of claim 32 wherein said concentrate is in the form of an essentially dry powder.

52. The concentrate of claim 32 wherein said concentrate is in the form of a tablet.

53. An essentially dry mixture suitable for constituting with water, carbonated or non-carbonated, to form a final beverage for oral administration of water, physiologically essential electrolytes, nutrient minerals, and carbohydrates to a human body, said dry mixture comprising:
- from about 0.4 to about 0.8 ppm of iron;
- from about 8 to about 12 meq. of a potassium cation component per liter of said final aqueous beverage;
- from about 8 to about 12 meq. of a sodium cation component per liter of said final aqueous beverage;
- from about 75 to about 200 mg of Vitamin C per liter of said final aqueous beverage;
- from about 20 to about 60 I.U. of Vitamin E per liter of said final aqueous beverage;
- from about 1 to about 5 weight percent, based on the total weight of said final aqueous beverage, of crystalline fructose;
- from about 3 to about 6 weight percent, based on the total weight of said final aqueous beverage, of maltodextrin;
- a sufficient amount of an edible acid component such that when said essentially dry mixture is constituted with said water to give said final beverage the pH of said final aqueous beverage is in a range of from about 2 to about 6.5; and
- said final aqueous beverage having an osmolality of from about 100 to about 270 mOs/l.

54. The essentially dry mixture of claim 53 further comprising Vitamin $B_{12}$.

55. The essentially dry mixture of claim 54 wherein said Vitamin $B_{12}$ is present in an amount ranging from about 1 to about 5 micrograms per liter of said final aqueous beverage.

56. The essentially dry mixture of claim 53 further comprising caffeine.

57. The essentially dry mixture of claim 56 wherein said caffeine is present in an amount ranging from about 100 to about 200 mg per liter of said final aqueous beverage.

58. An essentially dry mixture suitable for constituting with water, carbonated or non-carbonated, to form a final beverage for oral administration of water, physiologically essential electrolytes, nutrient minerals, and carbohydrates to a human body, comprising:
- from about 0.5 to about 0.7 ppm of iron;
- from about 9 to about 11 meq. of a potassium cation component per liter of said final aqueous beverage;
- from about 9 to about 11 meq. of a sodium cation component per liter of said final aqueous beverage;
- from about 5 to about 7 meq. of a calcium cation component per liter of said final aqueous beverage;
- from about 9 to about 11 meq. of a chloride anion component per liter of said final aqueous beverage;
- from about 10 to about 14 meq. of a phosphate anion component per liter of said final aqueous beverage;
- from about 1 to about 3 meq. of a magnesium cation component per liter of said final aqueous beverage;
- from about 10 to about 14 meq. of a bicarbonate anion component per liter of said final aqueous beverage;
- from about 80 to about 120 mg of Vitamin C per liter of said final aqueous beverage;
- from about 30 to about 50 I.U. of Vitamin E per liter of said final aqueous beverage;
- from about 1 to about 2 weight percent, based on the total weight of said final aqueous beverage, of crystalline fructose;
- from about 3 to about 6 weight percent, based on the total weight of said final aqueous beverage, of maltodextrin;
- a sufficient amount of an edible acid component such that when said essentially dry mixture is constituted with said water to give said final aqueous beverage, the pH of said final aqueous beverage is in the range of from about 3 to about 6; and
- said final aqueous beverage having an osmolality of from about 200 to about 290 mOs/l.

* * * * *